(12) United States Patent
Kanefsky et al.

(10) Patent No.: US 12,260,942 B1
(45) Date of Patent: *Mar. 25, 2025

(54) TECHNOLOGY FOR AUTOMATICALLY PROCESSING PRESCRIPTION FUNCTIONALITIES BASED ON TRANSMITTED DIGITAL IMAGES

(71) Applicant: WALGREEN CO., Deerfield, IL (US)

(72) Inventors: Lindsey Kanefsky, Chicago, IL (US); Kartik Subramanian, Chicago, IL (US); Dimple Rao, Chicago, IL (US)

(73) Assignee: WALGREEN CO., Deerfield, IL (US)

( * ) Notice: Subject to any disclaimer, the term of this patent is extended or adjusted under 35 U.S.C. 154(b) by 192 days.

This patent is subject to a terminal disclaimer.

(21) Appl. No.: 17/319,034

(22) Filed: May 12, 2021

Related U.S. Application Data (63) Continuation of application No. 15/422,227, filed on Feb. 1, 2017, now Pat. No. 11,074,320.

(51) Int. Cl.
*G16H 10/60* (2018.01)
*G16H 20/10* (2018.01)
*G16H 30/00* (2018.01)

(52) U.S. Cl.
CPC ............. *G16H 20/10* (2018.01); *G16H 30/00* (2018.01)

(58) Field of Classification Search
CPC ............................. G16H 20/10; G16H 30/00
See application file for complete search history.

(56) References Cited

U.S. PATENT DOCUMENTS

| | | |
|---|---|---|
| 10,366,784 B1 | 7/2019 | Eller |
| 10,552,575 B1 | 2/2020 | Mohebbi et al. |
| 2009/0006126 A1* | 1/2009 | Champigny ........... G16H 20/10 705/2 |
| 2015/0161351 A1 | 6/2015 | Scalpati |
| 2016/0306936 A1 | 10/2016 | Mizobe |
| 2017/0093832 A1* | 3/2017 | Schwartz ................ H04L 63/08 |
| 2021/0074416 A1* | 3/2021 | Iantorno ............... A61J 7/0084 |

* cited by examiner

Primary Examiner — Maroun P Kanaan
(74) Attorney, Agent, or Firm — MARSHALL, GERSTEIN & BORUN LLP; Randall G. Rueth (57) ABSTRACT

Systems and methods for automatically processing prescription refills and transfers are disclosed. According to certain aspects, a server associated with a pharmacy may receive, from an electronic device, a message including a digital image depicting a container of a prescription. The server may analyze the digital image to identify a set of visual identifiers depicted in the digital image. Based on the set of visual identifiers, the server may determine whether the prescription is associated with the pharmacy and, based on the determination, may facilitate either a refill of the prescription or a transfer of the prescription to the pharmacy.

16 Claims, 6 Drawing Sheets

TECHNOLOGY FOR AUTOMATICALLY PROCESSING PRESCRIPTION FUNCTIONALITIES BASED ON TRANSMITTED DIGITAL IMAGES

CROSS-REFERENCE TO RELATED APPLICATIONS

This application is a continuation of U.S. patent application Ser. No. 15/422,227, filed Feb. 1, 2017, which is hereby incorporated by reference in its entirety.

FIELD

The present disclosure is directed to processing prescription functionalities. More particularly, the present disclosure is directed to systems and methods for automatically processing prescription refill and transfer functionalities based on analyzing digital images transmitted by electronic devices.

BACKGROUND

Individuals have medication prescriptions to treat a variety of ailments or conditions, where the prescriptions are authorized or given by medical personnel such as doctors. Typically, a prescription for a given medication may be authorized for one or more refills when the original prescription expires or is exhausted, and an individual having a prescription may have the prescription refilled at the pharmacy that originally filled the prescription. Alternatively, individuals having prescriptions may be able to transfer prescriptions from one pharmacy to another pharmacy.

However, obtaining a prescription refill or initiating a prescription transfer can often be time consuming and inconvenient. In one scenario, an individual may be required to call a pharmacy or physician to request a refill or transfer. In other scenario, an individual may be required to physically visit a pharmacy to request and obtain a refill or transfer, which is time consuming. In a further scenario, a pharmacy may require an individual to download and install proprietary software (e.g., an application) in order to remotely request a refill or transfer, or log onto a website through which the individual may request a refill or transfer.

Accordingly, there is an opportunity for technology to enable individuals to efficiently and effectively order a prescription refill or initiate a prescription transfer using an electronic device.

SUMMARY

In an embodiment, a computer-implemented method of processing refills of prescriptions associated with a pharmacy is provided. The method may include receiving, via a network connection at a server associated with the pharmacy, an electronic message originating from an electronic device of a user, the electronic message comprising a digital image of a container associated with a prescription, analyzing, by a computer processor, the digital image to identify a set of visual identifiers depicted in the digital image, determining, based on the set of visual identifiers, that the prescription is associated with the pharmacy, and in response to determining that the prescription is associated with the pharmacy, processing a refill for the prescription.

In another embodiment, a computer-implemented method of processing prescription transfers is provided. The method may include receiving, via a network connection at a server associated with a pharmacy, an electronic message originating from an electronic device of a user, the electronic message comprising a digital image of a container associated with a prescription, analyzing, by a computer processor, the digital image to identify a set of visual identifiers depicted in the digital image, determining, based on the set of visual identifiers, that the prescription is not associated with the pharmacy, and in response to determining that the prescription is not associated with the pharmacy: transmitting, to the electronic device via the network connection, a location request, receiving, from the electronic device via the network connection, a specified location, determining, based on the specified location, a retail location of the pharmacy, and processing a transfer of the prescription to the retail location of the pharmacy.

In a further embodiment, a system for processing prescriptions associated with a pharmacy is provided. The system may include a transceiver configured to communicate via at least one network connection, a memory configured to store (i) a set of reference visual identifiers associated with the pharmacy, and (ii) non-transitory computer executable instructions, and a processor configured to interface with the transceiver and the memory. The processor is configured to execute the non-transitory computer executable instructions to cause the processor to: receive, via the transceiver, an electronic message originating from an electronic device of a user, the electronic message comprising a digital image of a container associated with a prescription, analyze the digital image to identify a set of visual identifiers depicted in the digital image, access, from the memory, the set of reference visual identifiers associated with the pharmacy, compare the set of visual identifiers to the set of reference visual identifiers, based on the comparing, calculate a similarity score between the set of visual identifiers and the set of reference visual identifiers, determine whether the similarity score at least meets a threshold value, and based on the determining, processing (i) a refill for the prescription, or (ii) a transfer of the prescription to a retail location of the pharmacy.

DETAILED DESCRIPTION

The present embodiments may relate to, inter alia, technology for processing refills or transfers of prescriptions using information transmitted in electronic messages. According to certain aspects, a user may use an electronic device to transmit a digital image to a back-end server associated with a pharmacy, where the digital image depicts a container (e.g., a vial) corresponding to a prescription. The back-end server may analyze the digital image to identify a set of visual identifiers that are depicted on or in association with the prescription container. Based on the set of visual identifiers, the back-end server may determine whether the corresponding prescription is associated with the pharmacy or with another pharmacy.

If the back-end server determines that the corresponding prescription is associated with the pharmacy, the back-end server may request confirmation that the user wishes to have the prescription refilled at a certain retail location of the pharmacy. In contrast, if the back-end server determines that the corresponding prescription is associated with an alternative pharmacy, the back-end server may process a transfer of the prescription from the alternative pharmacy to the pharmacy.

The systems and methods therefore offer numerous benefits. In particular, the systems and methods enable users with a seamless and effective way to initiate prescription refills and transfers by sending digital images. In this regard, users are not confined to manually initiating prescription refills and transfers, or downloading proprietary applications associated with pharmacies. Instead, users may directly communicate with a pharmacy via sending and receiving electronic messages. Further, the systems and methods enable retail stores with additional marketing techniques in an effort to drive traffic through the retail stores. In particular, the retail stores may locate signage throughout the retail stores that encourages customers to initiate prescription refills and transfers via sending electronic messages. It should be appreciated that additional benefits are envisioned.

The systems and methods discussed herein address a challenge that is particular to prescription management. In particular, the challenge relates to a difficulty in facilitating refills and transfers of prescription medications for customers. Conventionally, customers request prescription refills or transfers through in-person visits, telephone calls, or through proprietary applications that must be separately downloaded. However, these channels are cumbersome and sometimes involve human error. The systems and methods offer improved capabilities to solve these problems by enabling customers to transmit messages including digital images depicting prescriptions, and enabling customers to communicate with a pharmacy via an electronic messaging channel. Further, because the systems and methods employ the capture, analysis, and transmission of data between and among multiple devices, the systems and methods are necessarily rooted in computer technology in order to overcome the noted shortcomings that specifically arise in the realm of prescription management.

According to implementations, the systems and methods may support a dynamic, real-time or near-real-time communication, analysis, and processing of data. In particular, the systems and methods may receive electronic messages from electronic devices in real-time or near real-time, automatically and dynamically analyze the electronic messages and content thereof, automatically and dynamically communicate with customers via electronic messages, and automatically and dynamically facilitate prescription refills and transfers, in real-time or near-real-time.

Figure 1:
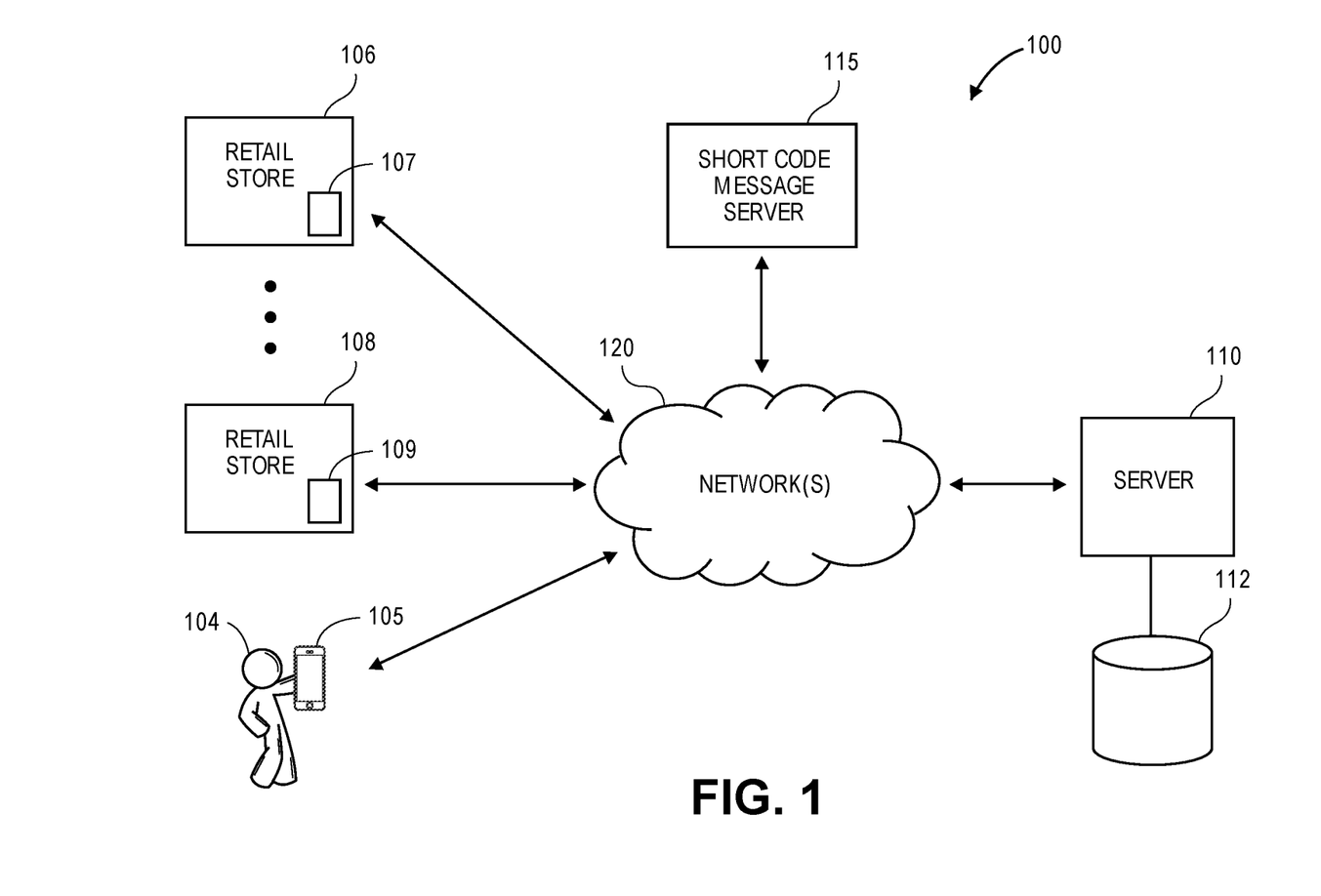
FIG. 1 depicts an overview of components and entities associated with the systems and methods, in accordance with some embodiments.

FIG. 1 illustrates an overview of a system 100 of components configured to facilitate the systems and methods. It should be appreciated that the system 100 is merely an example and that alternative or additional components are envisioned.

As illustrated in FIG. 1, the system 100 may include a user 104 or individual having or interacting with an electronic device 105. The user 104 may be any individual or person who may be interested in purchasing products or services that may be offered for sale by a set of retail stores 106, 108. In an embodiment, each of the set of retail stores 106, 108 may be associated with a retail location of a pharmacy. For example, the retail store 106 may be associated with example Pharmacy A and the retail store 108 may be associated with example Pharmacy B.

The electronic device 105 may be any type of electronic device such as a mobile device (e.g., a smartphone), notebook computer, tablet, phablet, GPS (Global Positioning System) or GPS-enabled device, smart watch, smart glasses, smart bracelet, wearable electronic, PDA (personal digital assistant), pager, computing device configured for wireless communication, and/or the like. The set of retail stores 106, 108 may include a respective set of computers 107, 109 or terminals associated therewith that may support a checkout procedure or a point of sale. In particular, the user 104 may purchase products or services from either of the retail stores 106, 108 through the use of the respective computer 107, 109. Although two (2) retail stores 106, 108 and computers 107, 109 are depicted in FIG. 1, it should be appreciated that other amounts are envisioned.

The electronic device 105 and the computers 107, 109 may communicate with a server 110 via one or more networks 120. The server 110 may be associated with a pharmacy, where the pharmacy may have a retail location(s) that is either or both of the set of retail stores 106, 108. In embodiments, the network(s) 120 may support any type of data communication via any standard or technology (e.g., GSM, CDMA, TDMA, WCDMA, LTE, EDGE, OFDM, GPRS, EV-DO, UWB, Internet, IEEE 802 including Ethernet, WiMAX, Wi-Fi, Bluetooth, and others). The server 110 may be configured to interface with or support a memory or storage 112 capable of storing various data. In one implementation, the storage 112 may include a database that stores account-related data and another database that stores prescription-related data.

The electronic device 105 may include an image sensor configured to capture digital images, and/or may be configured to store digital images. According to embodiments, the user 104 may use the electronic device 105 to capture, via the image sensor, a digital image that may depict a container (e.g., a vial or other component) associated with a prescription. Additionally or alternatively, the user 104 may use the electronic device 104 to select a digital image that may depict a container associated with a prescription, and select the digital image for inclusion in an electronic message, such as multimedia messaging service (MMS) message.

The electronic device 105 may transmit the electronic message to the server 110 via the network(s) 120. In an implementation, the electronic device 105 may specify a "short code" as the destination for the electronic message, in which case the electronic device 105 may transmit the electronic message to a short code message server 115 via the network(s) 120, where the short code message server 115 may forward the electronic message to the server 110 via the network(s) 120.

After receiving the electronic message, the server 110 may analyze the digital image included in the electronic message to identify a set of visual identifiers that may be depicted in the digital image. The server 110 may determine, from the set of visual identifiers, whether the prescription is associated with the pharmacy corresponding to the server 110. If the prescription is associated with the pharmacy, the server 110 may initiate prescription refill functionalities; and if the prescription is associated with an additional pharmacy, the server 110 may initiate prescription transfer functionalities to transfer the prescription from the additional pharmacy to the pharmacy.

To facilitate the prescription refill and transfer functionalities, the server 110 may generate and send electronic messages to the electronic device 105, and receive electronic messages from the electronic device 105. According to embodiments, the user 104 may use the electronic device 105 to specify and confirm information, such as location information, account information, transfer or refill confirmation, and/or other information. These functionalities are further discussed with respect to FIG. 2.

Figure 2:
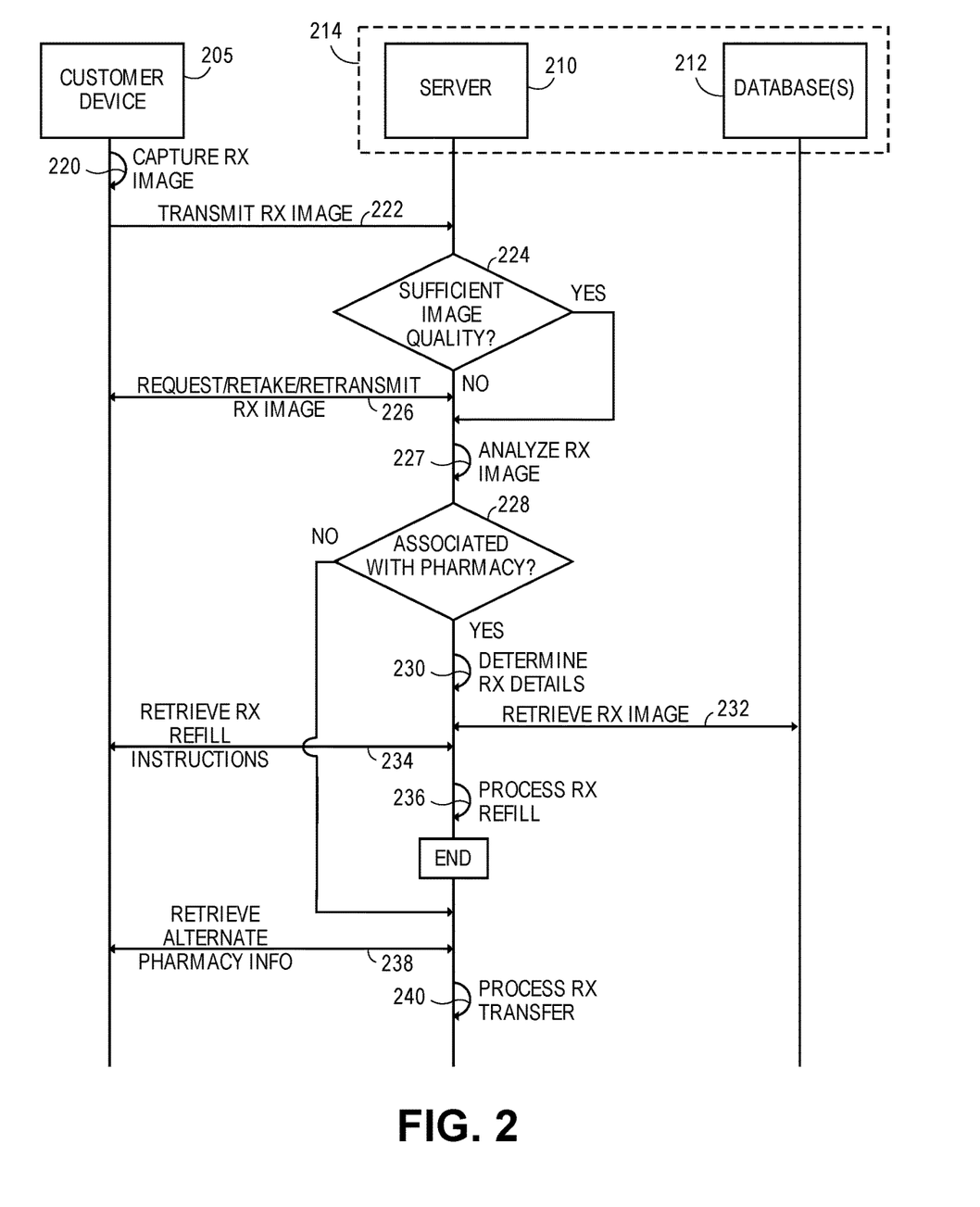
FIG. 2 depicts an example signal diagram associated with automatically processing prescriptions, in accordance with some embodiments.

FIG. 2 depicts a signal diagram 200 associated with processing prescriptions for a user or customer, in accordance with some embodiments. The signal diagram 200 includes a customer device 205 that may be operated by the customer (such as the electronic device 105 as discussed with respect to FIG. 1), a server 210 (such as the server 110 as discussed with respect to FIG. 1), and at least one database 212 (such as the database 112 as discussed with respect to FIG. 1). The server 210 and the database(s) 212 may be, in combination, a set of back-end components 214 that are remote from the customer device 205, where the set of back-end components 214 may be associated with a pharmacy having an associated set of retail pharmacy locations. It should be appreciated that additional or alternative components and devices are envisioned.

The signal diagram 200 may begin when the customer uses the customer device 205 to capture (220) one or more digital images of a prescription. In particular, the customer may use the customer device 205 to capture a digital image(s) of a container associated with a prescription medication. For example, the container may be a vial, box, tray, or other component that may hold or secure the medication. According to embodiments, the container may contain a set of visual identifiers such as one or more graphical objects, logos, text, barcodes, labels, and/or the like. Further, the container may have a certain size and shape. Additionally, the container may have a label that includes various information associated with the prescription, including but not limited to information associated with the patient (e.g., name, address, phone number, etc.), dosage and usage information, and refill information. In an implementation, the customer device 205 may prompt, via a user interface, the user to capture certain portions or angles of the container. In embodiments, the customer device 205 may receive or access the digital image(s) from another device or component, as an alternative to capturing the digital image(s).

After capturing or otherwise accessing the digital image (s), the customer device 205 may transmit (222) the digital image(s) of the prescription to the server 210 via a network connection. In embodiments, the customer device 205 may support an application into which the customer may select the captured digital image(s) (e.g., from a camera roll) as well as information for the destination. For example, the application may be a messaging application that may support SMS/MMS transmission (i.e., the digital image(s) is sent as part of an MMS message). It should be appreciated that other types of communication applications are envisioned.

In embodiments, the destination identification may identify the component or entity to which the digital image(s) is to be sent. For example, the destination may be a mobile station international subscriber directory number (MSISDN) associated with the server 210. For further example, the destination identification may be a short code associated with the server 210, in which case the digital image(s) may be routed to a short code message server, which may forward the digital image(s) to the server 210. It should be appreciated that other destination identifications are envisioned (e.g., telephone number, email address, website URL, etc.). For purposes of explanation, it may be assumed that the destination identification is associated with the server 210.

After receiving the digital image(s), the server 210 may determine (224) whether the digital image(s) is of sufficient image quality to identify certain visual indicators that may be depicted in the digital image(s). According to embodiments, the server 210 may employ one or more digital image analysis techniques, algorithms, routines, or the like to determine whether the digital image(s) depicts a prescription container, as well as assess and consider image characteristics such as sharpness, noise, range, tone reproduction, contrast, color accuracy, distortion, vignetting, exposure accuracy, lateral chromatic aberration (LCA), lens flare, color moire, and/or artifacts.

If the server 210 determines that the digital image(s) are of sufficient image quality ("YES"), processing may proceed to (227). In contrast, if the server 210 determines that the digital image(s) are not of sufficient image quality ("NO"), the server 210 may request (226) a new digital image(s). In particular, the server 210 may transmit a message to the customer device 205 via a network connection, where the message may include instructions for properly capturing digital image(s) that are of sufficient quality. Accordingly, the customer may use the customer device 205 to capture or access additional digital image(s) and transmit the additional digital image(s) to the server 210, at which point the server 210 may repeat (224) to determine whether the additional digital image(s) are of sufficient quality.

At 227, the server 210 may analyze the digital image(s) to identify a set of visual identifiers that may be depicted in the digital image(s), such as one or more graphical objects, logos, text, barcodes, labels, and/or the like. It should be appreciated that the server 210 may employ any type of image analysis technique, including an object recognition technique(s), in analyzing the digital image(s). According to embodiments, the pharmacy associated with the back-end components 214 may have certain visual identifiers on prescription containers that may be uniquely associated with the pharmacy. For example, a specific pharmacy may have a unique logo and position thereof, label shape/size, and color pattern for its containers.

Thus, in analyzing the digital image(s) in (227), the server 210 may determine whether any identified visual identifiers match or are similar to the visual identifiers for the pharmacy associated with the server 210. In particular, the server 210 may compare the identified visual identifier(s) to the visual identifier(s) for the pharmacy, where the server 210 may calculate a similarity score based on the comparison, and deem that the visual identifier(s) is a "match" if the calculated similarity score meets or exceeds a threshold amount or value. For example, if the server 210 calculates a similarity score of 85% and the threshold amount is 75%, then the server 210 may deem that the visual identifier(s) in the digital image(s) match those associated with the pharmacy. It should be appreciated that in comparing the visual identifier(s), the server 210 may employ any type of algorithm, calculation, technique, or the like.

At 228, the server 210 may determine whether the container depicted in the digital image(s) is associated with the pharmacy. More particularly, if the analysis in (227) results in the visual identifier(s) depicted in the digital image(s)

matching the visual identifier(s) associated with the pharmacy, then the server 210 may deem that the container depicted in the digital image(s) is associated with the pharmacy ("YES") and processing may proceed to (230). In contrast, if the analysis in (227) results in the visual identifier(s) depicted in the digital image(s) not matching the visual identifier(s) associated with the pharmacy, then the server 210 may deem that the container depicted in the digital image(s) is associated with an alternate pharmacy ("NO"), and processing may proceed to (238).

At (230), the server may initiate processing associated with facilitating a refill for the prescription. In particular, the server 210 may determine or identify details or information associated with the prescription depicted in the digital image(s) such as, but not limited to, a prescription number, patient information (e.g., name, address, phone number, etc.), and the like. In determining or identifying the details or information, the server 210 may perform one or more optical character recognition (OCR) techniques. In an embodiment, the server 210 may perform an OCR technique on a barcode that may be depicted in the digital image(s), where the output of the OCR technique may indicate certain details associated with the prescription (e.g., prescription number, patient information, etc.).

The database 212 may store up-to-date information associated with patient prescriptions. Accordingly, the server 210 may use the information determined in (230) to retrieve (232) additional information associated with the prescription from the database 212. For example, the server 210 may retrieve, for a prescription, data indicative of remaining refills available (i.e., whether the customer is eligible for a refill) and a preferred/default pickup location. In embodiments, the preferred/default pickup location may correspond to where the prescription was originally filled and/or where the customer picked up the most recent refill.

The server 210 may retrieve (234) prescription refill instructions from the customer device 205. In particular, the server 210 may query the customer device 205 to confirm refill instructions as well as the retail location for the refill. The customer may use the customer device 205 to confirm the prescription refill and the retail location for the refill, or may specify an alternate retail location for the refill (e.g., such as by entering a ZIP code or other location parameter). The server 210 may accordingly process (236) the prescription refill according to the specified information. In particular, the server 210 may transmit an instruction to the specified retail location to cause the prescription to be refilled at the specified retail location. Thus, the customer is able to pick up the prescription refill at the specified retail location, and processing may end.

If the server 210 determines in (228) that the prescription is associated with an alternate pharmacy, the server 210 may initiate prescription transfer functionalities (i.e., transferring the prescription from the alternate pharmacy to the pharmacy). In particular, the server 210 may retrieve (238) prescription refill instructions from the customer device 205. In particular, the server 210 may query the customer device 205 to confirm refill instructions as well as a desired location (e.g., ZIP code) or retail store location. The customer may use the customer device 205 to confirm the prescription refill and the retail location for the refill, or may otherwise specify a desired location. The server 210 may accordingly process (240) the prescription refill according to the specified information. In particular, the server 210 may determine, based on the desired location, a retail location of the pharmacy that may process the prescription refill. Further, the server 210 may transmit an instruction to the specified retail location to cause the prescription to be refilled at the specified retail location. In an implementation, the server 210 may transmit, to the specified retail location, one or more of the digital image(s) originally received from the customer device 205. Thus, the customer is able to pick up the prescription refill at the specified retail location, and processing may end.

FIGS. 3A-3C and 4A-4C illustrate example interfaces associated with the systems and methods. An electronic device (e.g., a mobile device, such as a smartphone) may be configured to display the interfaces and/or receive selections and inputs via the interfaces, where the electronic device may be associated with a user who may be a customer of a business, retail store, website, or the like. One or more dedicated applications that are configured to operate on the electronic device may display the interfaces. It should be appreciated that the interfaces are merely examples and that alternative or additional content is envisioned.

Figure 3A:
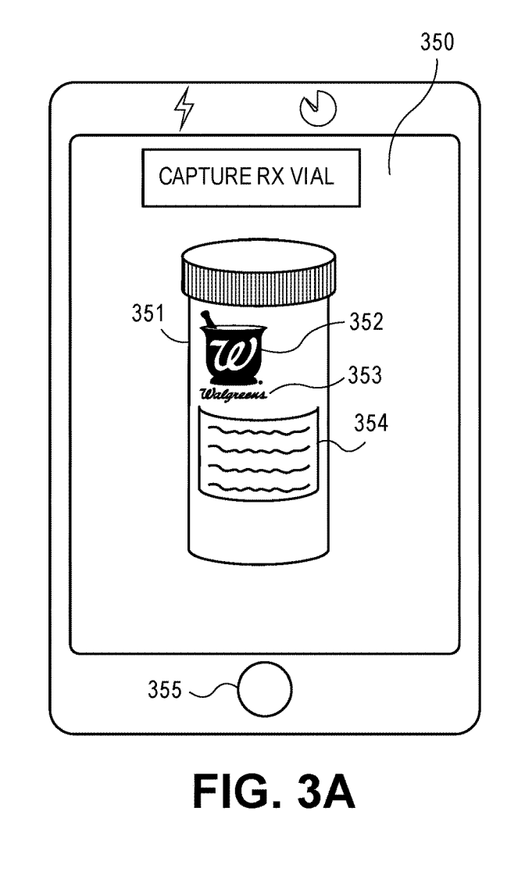
FIGS. 3A-3C depict example user interfaces associated with processing a prescription refill, in accordance with some embodiments.

FIG. 3A illustrates an interface 350 depicting a digital image capture application (i.e., a camera application) of the electronic device. The interface 350 may instruct the user to capture an image of a prescription container 351 (as shown: "Capture Rx Vial"). The user may position the prescription container 351 in the "live view" portion of the interface 350 and may select a shutter selection 355 to cause the electronic device to capture a digital image of the prescription container 351. As depicted in FIG. 3A, the prescription container 351 may include a set of visual identifiers including a logo 352, a pharmacy name 353, and a prescription label 354.

Figure 3B:
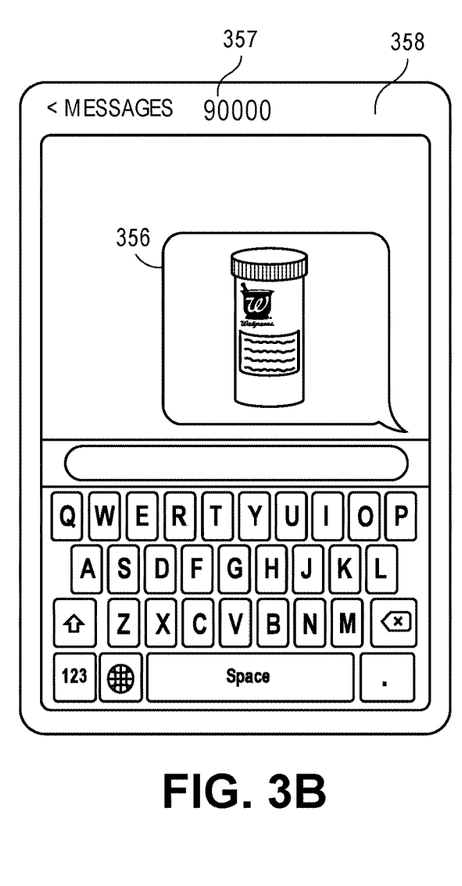

FIG. 3B illustrates an interface 358 depicting a communication application of the electronic device and a message transmission therein. In particular, the interface 358 depicts a message 356 that was transmitted to destination "90000" (357) (i.e., a short code), where the message 356 is in the form of a digital image as captured by the image capture application depicted in FIG. 3A. According to embodiments, the user may select the digital image of the message 356 via an image selection technique, as known in the art.

In the particular scenario depicted in FIG. 3B, the destination 357 may be associated with a pharmacy that filled the prescription indicated in the message 356. As a result, the pharmacy may receive the message 356, analyze the digital image included in the message 356, determine that the prescription container 351 is associated with the pharmacy, and thus determine that the user is requesting a refill of the prescription.

Figure 3C:
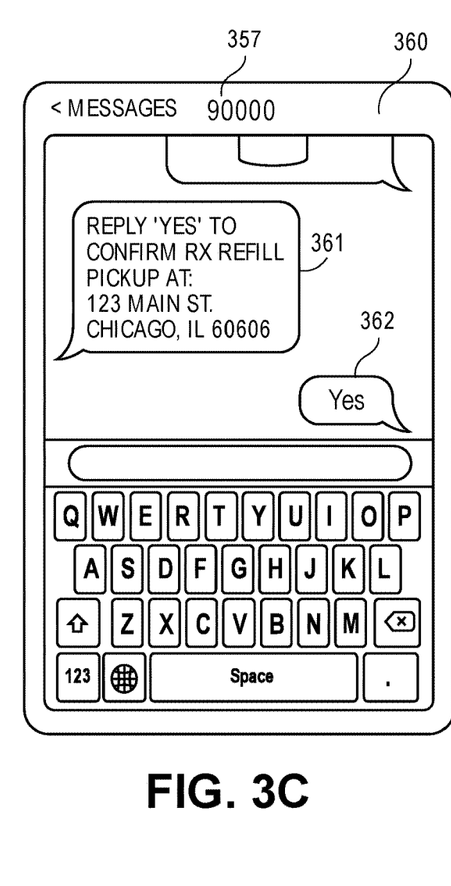

FIG. 3C illustrates an additional interface 360 depicting the communication application. In embodiments, after the pharmacy determines that the prescription depicted in the message 356 was filled by the pharmacy, the pharmacy may generate and transmit a response message 361 that the electronic device may display. As depicted in FIG. 3C, the response message 361 requests confirmation of a location for pickup of a prescription refill. The user may use the communication application to input a confirmation message 362 (as shown, "Yes"), and the communication application may transmit the confirmation message 362 to the destination 357, after which the pharmacy may process the prescription refill.

Figure 4A:
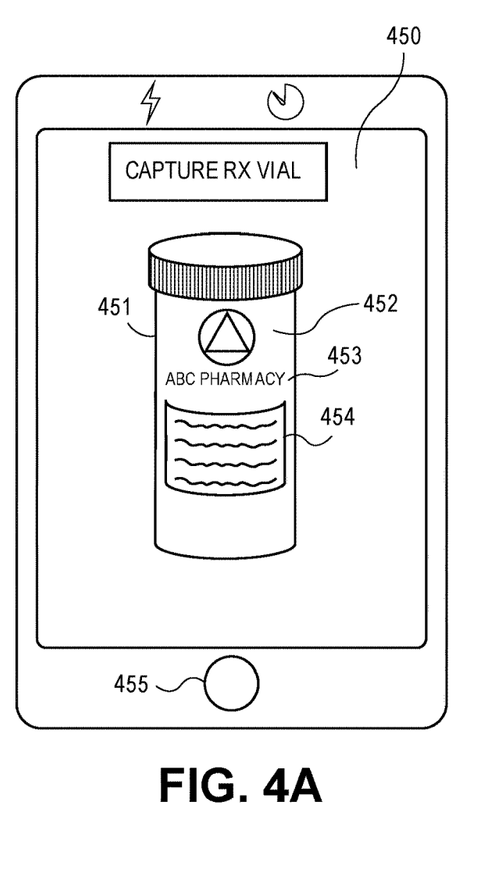
FIGS. 4A-4C depict example user interfaces associated with processing a prescription transfer, in accordance with some embodiments.

FIG. 4A illustrates an interface 450 depicting a digital image capture application (i.e., a camera application) of the electronic device. The interface 450 may instruct the user to capture an image of a prescription container 451 (as shown: "Capture Rx Vial"). The user may position the prescription container 451 in the "live view" portion of the interface 450 and may select a shutter selection 455 to cause the electronic device to capture a digital image of the prescription container 451. As depicted in FIG. 4A, the prescription container 451 may include a set of visual identifiers including a logo 452, a pharmacy name 453, and a prescription label 454.

Figure 4B:
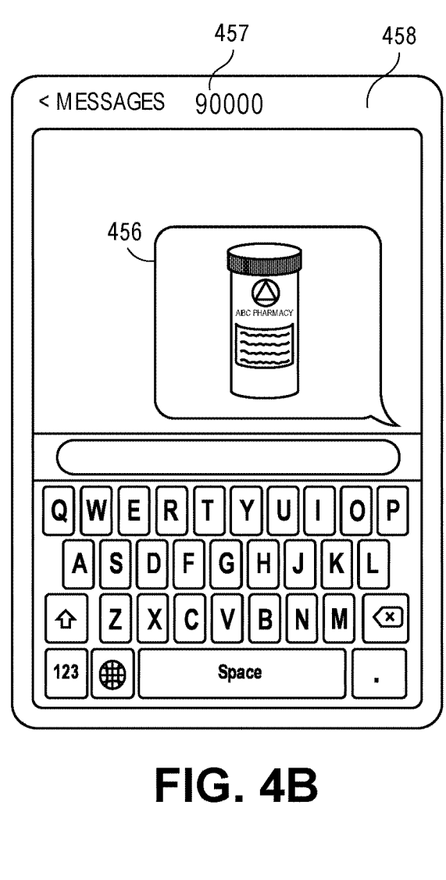

FIG. 4B illustrates an interface 458 depicting a communication application of the electronic device and a message transmission therein. In particular, the interface 458 depicts a message 456 that was transmitted to destination "90000" (457) (i.e., a short code), where the message 456 is in the form of a digital image as captured by the image capture application depicted in FIG. 4A. According to embodiments, the user may select the digital image of the message 456 via an image selection technique, as known in the art.

In the particular scenario depicted in FIG. 4B, the destination 457 is associated with a pharmacy that did not fill the prescription indicated in the message 456. As a result, the pharmacy may receive the message 456, analyze the digital image included in the message 456, determine that the prescription container 451 is associated with another pharmacy, and thus determine that the user is requesting a transfer of the prescription to the pharmacy.

Figure 4C:
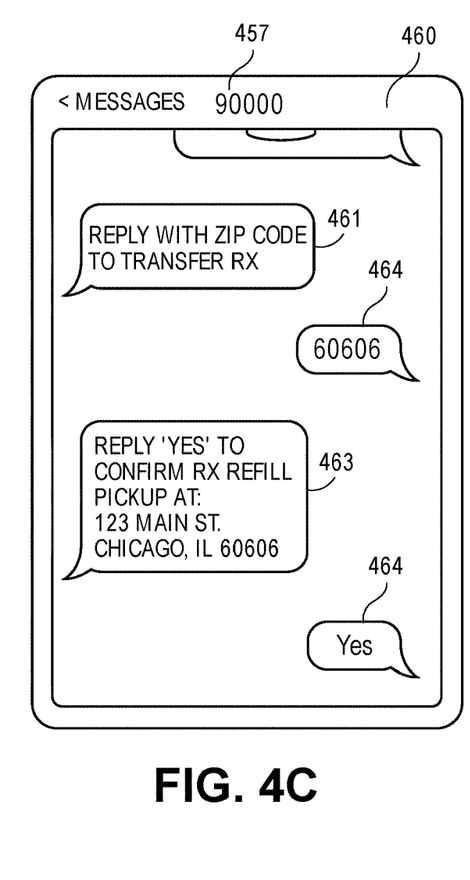

FIG. 4C illustrates an additional interface 460 depicting the communication application. In embodiments, after the pharmacy determines that the prescription depicted in the message 456 was not filled by the pharmacy, the pharmacy may generate and transmit a first response message 461 that the electronic device may display. As depicted in FIG. 4C, the first response message 461 requests that the user enter a ZIP code corresponding to a desired transfer location. The user may use the communication to input a location message 462 (as shown "60606"), and the communication application may transmit the location message 462 to the destination 457. The pharmacy may process the content of the location message 462 and transmit a second response message 463 that the electronic device may display. As depicted in FIG. 4C, the second response message 463 requests confirmation of a location for transfer of the prescription. The user may use the communication application to input a confirmation message 464 (as shown, "Yes"), and the communication application may transmit the confirmation message 464 to the destination 457, after which the pharmacy may process the transfer of the prescription.

Figure 5:
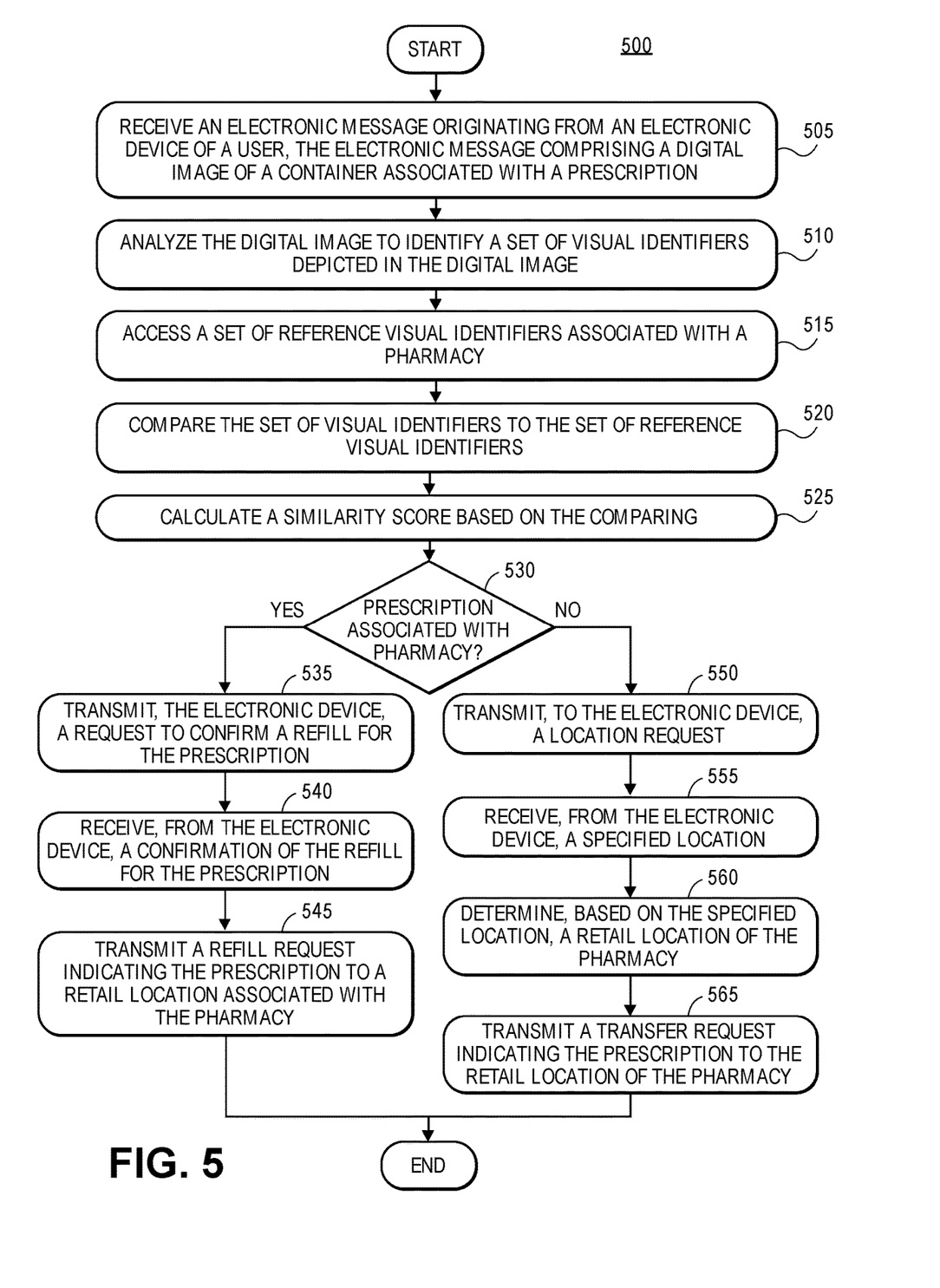
FIG. 5 depicts an example flow diagram associated with processing prescriptions, in accordance with some embodiments.

FIG. 5 depicts is a block diagram of an example method 500 of processing prescriptions. The method 500 may be facilitated by a server (such as the server 210 as discussed with respect to FIG. 2) that may be in communication with an electronic device of a user (such as the customer device 205 as discussed with respect to FIG. 2).

The method 500 may begin when the server receives (block 505), via a network connection, an electronic message originating from an electronic device of a user, where the electronic message may comprise a digital image of a container associated with a prescription. In embodiments, the server may receive the electronic message in the form of an MMS message via a cellular network connection. Additionally or alternatively, the electronic device may send the MMS message to a short code message server, which may forward the MMS message to the server. It should be appreciated that other types of connections and message generation applications or platforms are envisioned.

The server may analyze (block 510) the digital image to identify a set of visual identifiers depicted in the digital image. According to embodiments, the set of visual identifiers may be visual logos, graphical objects, alphanumeric text, and/or other content. The server may access (block 515) a set of reference visual identifiers associated with the pharmacy. In particular, the set of reference visual identifiers may be visual logos, graphical objects, alphanumeric text, and/or other content that may be associated with the pharmacy.

The server may compare (block 520) the set of visual identifiers depicted in the digital image to the set of reference visual identifiers. In operation, the server may use any type of image analysis technique, algorithm, or the like. As a result of the comparison, the server may calculate (block 525) a similarity score. According to embodiments, the similarity score may reflect a degree of similarity between the set of visual identifiers and the set of reference visual identifiers.

The server may determine (block 530) whether the prescription is associated with the pharmacy. In particular, the server may determine whether the calculated similarity score at least meets a threshold value. If the calculated similarity score at least meets a threshold value, then the server may deem that the prescription is associated with the pharmacy ("YES"), and processing may proceed to (block 535). In contrast, if the calculated similarity score does not meet a threshold value, then the server may deem that the prescription is not associated with the pharmacy ("NO"), and processing may proceed to (block 550).

At block 535, the server may facilitate prescription refill functionalities. In particular, the server may transmit, to the electronic device, a request to confirm a refill for the prescription. The user of the electronic device may use the electronic device to either confirm or reject a prescription refill. At block 540, the server may receive, from the electronic device, a confirmation of the refill for the prescription. In embodiments, the confirmation may include a selection of a retail location from which the user prefers to pick up the prescription refill. As a result, the server may transmit (block 545) a refill request indicating the prescription to the retail location associated with the pharmacy. Thus, the retail location may process the refill and the user may pick up the prescription refill from the retail location. Processing may then end or proceed to other functionality.

At block 550, the server may facilitate prescription transfer functionalities. In particular, the server may transmit, to the electronic device, a location request. In particular, the location request may query a ZIP code (or other location-based parameter) for the user of the electronic device to enter. The server may receive (block 555), from the electronic device, a specified location. In embodiments, the specified location may be a ZIP code or other location-based parameter.

The server may determine (block 560), based on the specified location, a retail location of the pharmacy. In particular, the server may determine a retail location of the pharmacy that is proximate to the specified location. In embodiments, the server may transmit, to the electronic device, a request to confirm transfer of the prescription to the retail location of the pharmacy. The server may transmit (block 565) a transfer request indicating the prescription to the retail location of the pharmacy. In embodiments, the server may transmit, to the retail location, the digital image and/or any information that the server identified from the digital image. In this regard, the retail location may process transfer of the prescription and may facilitate other functionalities accordingly.

Figure 6:
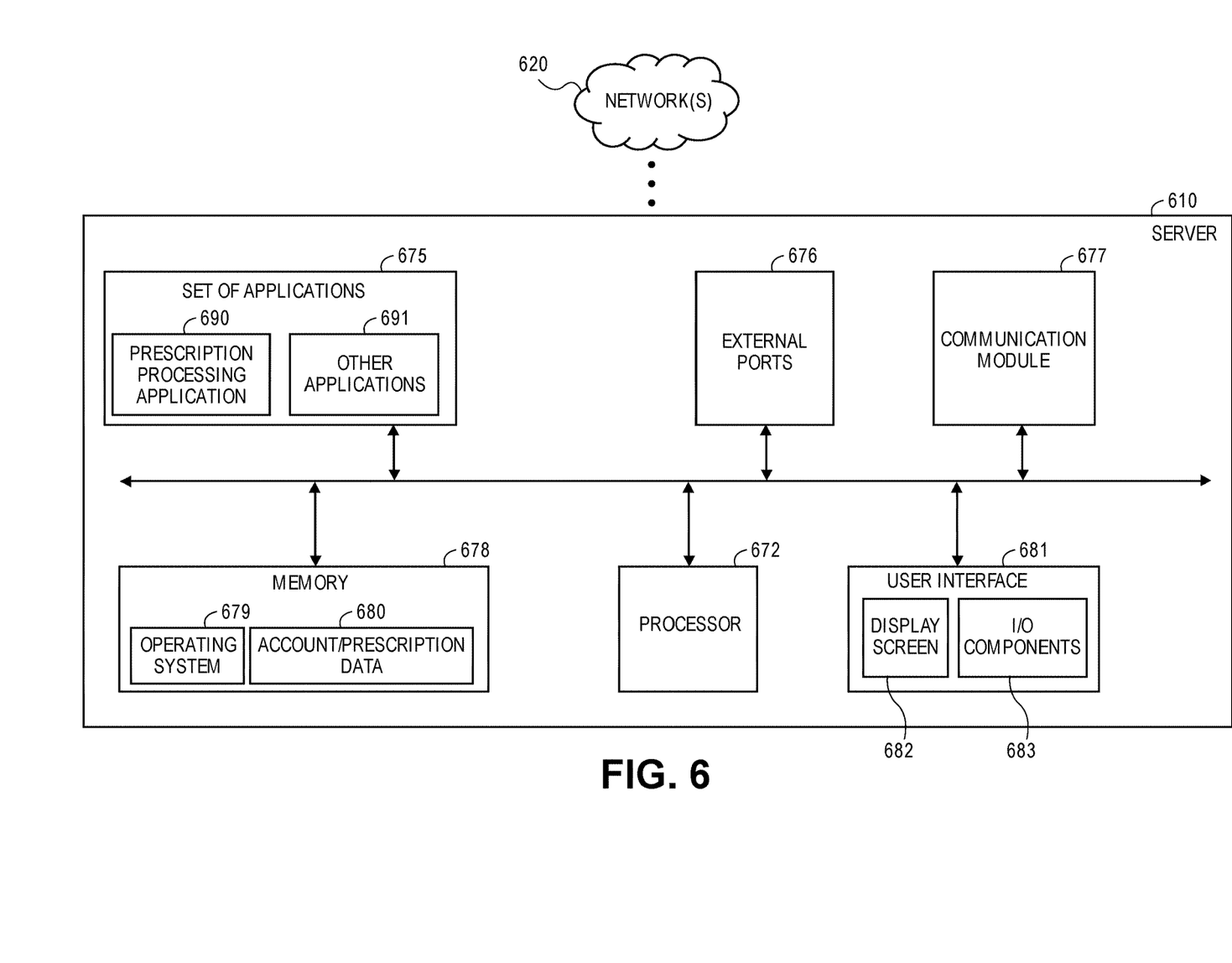
FIG. 6 is a block diagram of an example server, in accordance with some embodiments.

FIG. 6 illustrates a diagram of an example server 610 (such as the server 210 as discussed with respect to FIG. 2) in which the functionalities as discussed herein may be implemented. It should be appreciated that the server 610 may be associated with a pharmacy having one or more retail stores.

The server 610 may include a processor 672 as well as a memory 678. The memory 678 may store an operating system 679 capable of facilitating the functionalities as discussed herein as well as a set of applications 675 (i.e., machine readable instructions). For example, one of the set of applications 675 may be a prescription processing application 690 configured to facilitate refills and transfers of prescriptions. It should be appreciated that one or more other applications 691 are envisioned.

The processor 672 may interface with the memory 678 to execute the operating system 679 and the set of applications 675. According to some embodiments, the memory 678 may also include account/prescription data 680 including data related to user accounts and prescriptions of users. The memory 678 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others.

The server 610 may further include a communication module 677 configured to communicate data via one or more networks 620. According to some embodiments, the communication module 677 may include one or more transceivers (e.g., WWAN, WLAN, and/or WPAN transceivers) functioning in accordance with IEEE standards, 3GPP standards, or other standards, and configured to receive and transmit data via one or more external ports 676. For example, the communication module 677 may receive, from an electronic device via the network 620, a message including a digital image. For further example, the communication module 677 may transmit, to the electronic device via the network 620, a confirmation message indicating prescription refill or transfer instructions.

The server 610 may further include a user interface 681 configured to present information to a user and/or receive inputs from the user. As shown in FIG. 6, the user interface 681 may include a display screen 682 and I/O components 683 (e.g., ports, capacitive or resistive touch sensitive input panels, keys, buttons, lights, LEDs, speakers, microphones). According to some embodiments, the user may access the server 610 via the user interface 681 to review information and/or perform other functions. In some embodiments, the server 610 may perform the functionalities as discussed herein as part of a "cloud" network or may otherwise communicate with other hardware or software components within the cloud to send, retrieve, or otherwise analyze data.

In general, a computer program product in accordance with an embodiment may include a computer usable storage medium (e.g., standard random access memory (RAM), an optical disc, a universal serial bus (USB) drive, or the like) having computer-readable program code embodied therein, wherein the computer-readable program code may be adapted to be executed by the processor 672 (e.g., working in connection with the operating system 679) to facilitate the functions as described herein. In this regard, the program code may be implemented in any desired language, and may be implemented as machine code, assembly code, byte code, interpretable source code or the like (e.g., via C, C++, Java, Actionscript, Objective-C, Javascript, CSS, XML). In some embodiments, the computer program product may be part of a cloud network of resources.

Although the following text sets forth a detailed description of numerous different embodiments, it should be understood that the legal scope of the invention may be defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that may be permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that may be temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules may provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it may be communicatively coupled. A further hardware module may then, at a later time, access the memory device to retrieve and process the stored output. Hardware modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment, or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment may be included in at least one embodiment. The appearances of the phrase "in one embodiment" in various places in the specification are not necessarily all referring to the same embodiment.

As used herein, the terms "comprises," "comprising," "may include," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also may include the plural unless it is obvious that it is meant otherwise.

This detailed description is to be construed as examples and does not describe every possible embodiment, as describing every possible embodiment would be impractical, if not impossible. One could implement numerous alternate embodiments, using either current technology or technology developed after the filing date of this application.

What is claimed is:

1. A computer-implemented method of processing prescription transfers, the method comprising:

receiving, within a message transmission session via a network connection at a server associated with a pharmacy, an electronic message originating from an electronic device of a user, the electronic message comprising a digital image;

analyzing, by a computer processor using an image analysis technique, the digital image to determine that the digital image depicts a container associated with a prescription;

in response to determining that the digital image depicts the container associated with the prescription, analyzing, by a computer processor, the digital image to identify (i) alphanumeric text included on a label on the container, and (ii) a logo on the container separate from the label;

based on the analyzing, determining, without input from the user, that the user is requesting a transfer of the prescription to the pharmacy based on the prescription not being associated with the pharmacy; and in response to determining that the user is requesting the transfer of the prescription to the pharmacy, and within the message transmission session:

transmitting, to the electronic device, a first response message comprising information associated with initiating the transfer of the prescription, wherein the user inputs a location via the electronic device, receiving, from the electronic device, a message identifying the location, transmitting, to the electronic device, a second response message that requests confirmation of a retail location of the pharmacy associated with the location identified in the message, receiving, from the electronic device, a confirmation message, and in response to receiving the confirmation message, processing the transfer of the prescription to the retail location of the pharmacy associated with the location.

2. The computer-implemented method of claim 1, further comprising:
comparing, by the computer processor, (i) the alphanumeric text to reference alphanumeric text, and (ii) the logo to a reference logo.

3. The computer-implemented method of claim 2, further comprising:
accessing, from memory, at least two reference visual identifiers associated with the pharmacy, wherein one of the at least two reference visual identifiers is the reference logo and another of the at least two reference visual identifiers is the reference alphanumeric text.

4. The computer-implemented method of claim 2, wherein comparing the logo to the reference logo comprises:
calculating a similarity score between the logo and the reference logo; and
determining that the similarity score at least meets a threshold value.

5. The computer-implemented method of claim 1, wherein processing the transfer of the prescription to the retail location of the pharmacy comprises:
transmitting a transfer request indicating the prescription to the retail location of the pharmacy.

6. A system for processing prescription transfers to a pharmacy, comprising:
a transceiver configured to communicate via at least one network connection; and
a processor interfacing with the transceiver and configured to:
receive, via the transceiver within a message transmission session, an electronic message originating from an electronic device of a user, the electronic message comprising a digital image,
analyze, using an image analysis technique, the digital image to determine that the digital image depicts a container associated with a prescription,
in response to determining that the digital image depicts the container associated with the prescription, analyze the digital image to identify (i) alphanumeric text included on a label on the container, and (ii) a logo on the container separate from the label,
based on the analyzing, determine, without input from the user, that the user is requesting a transfer of the prescription to the pharmacy based on the prescription not being associated with the pharmacy, and
in response to determining that the user is requesting the transfer of the prescription to the pharmacy, and within the message transmission session:
transmit, to the electronic device via the transceiver, a first response message comprising information associated with initiating the transfer of the prescription, wherein the user inputs a location via the electronic device,
receive, from the electronic device via the transceiver, a message identifying the location,
transmit, to the electronic device via the transceiver, a second response message that requests confirmation of a retail location of the pharmacy associated with the location identified in the message,
receive, from the electronic device via the transceiver, a confirmation message, and
in response to receiving the confirmation message, process the transfer of the prescription to the retail location of the pharmacy associated with the location.

7. The system of claim 6, wherein the processor is further configured to:
compare (i) the alphanumeric text to reference alphanumeric text, and (ii) the logo to a reference logo.

8. The system of claim 7, further comprising:
a memory storing (i) a reference logo associated with the pharmacy, and (ii) reference alphanumeric text associated with the pharmacy;
and wherein the processor is further configured to:
accessing, from the memory, the reference logo and the reference alphanumeric text.

9. The system of claim 7, wherein to compare the logo to the reference logo, the processor is configured to:
calculate a similarity score between the logo and the reference logo, and determine that the similarity score at least meets a threshold value.

10. The system of claim 6, wherein to process the transfer of the prescription to the retail location of the pharmacy, the processor is configured to:
transmit a transfer request indicating the prescription to the retail location of the pharmacy.

11. A non-transitory computer-readable storage medium configured to store instructions, the instructions when executed by a processor causing the processor to perform operations comprising:
receiving, within a message transmission session via a network connection at a server associated with a pharmacy, an electronic message originating from an electronic device of a user, the electronic message comprising a digital image;
analyzing, using an image analysis technique, the digital image to determine that the digital image depicts a container associated with a prescription;
in response to determining that the digital image depicts the container associated with the prescription, analyzing the digital image to identify (i) alphanumeric text included on a label on the container, and (ii) a logo on the container separate from the label;
based on the analyzing, determining, without input from the user, that the user is requesting a transfer of the prescription to the pharmacy based on the prescription not being associated with the pharmacy; and
in response to determining that the user is requesting the transfer of the prescription to the pharmacy, and within the message transmission session:
transmitting, to the electronic device, a first response message comprising information associated with initiating the transfer of the prescription, wherein the user inputs a location via the electronic device,
receiving, from the electronic device, a message identifying the location,
transmitting, to the electronic device, a second response message that requests confirmation of a retail location of the pharmacy associated with the location identified in the message,
receiving, from the electronic device, a confirmation message, and
in response to receiving the confirmation message, processing the transfer of the prescription to the retail location of the pharmacy associated with the location.

12. The non-transitory computer-readable storage medium of claim 11, wherein the instructions when executed by a processor cause the processor to perform operations further comprising:

comparing (i) the alphanumeric text to reference alphanumeric text, and (ii) the logo to a reference logo.

13. The non-transitory computer-readable storage medium of claim 12, wherein the instructions when executed by the processor cause the processor to perform operations further comprising:

accessing, from memory, at least two reference visual identifiers associated with the pharmacy, wherein one of the at least two reference visual identifiers is the reference logo and another of the at least two reference visual identifiers is the reference alphanumeric text.

14. The non-transitory computer-readable storage medium of claim 12, wherein comparing the logo to the reference logo comprises:

calculating a similarity score between the logo and the reference logo; and determining that the similarity score at least meets a threshold value.

15. The non-transitory computer-readable storage medium of claim 11, wherein the instructions when executed by the processor cause the processor to perform operations further comprising:

in response to determining that the prescription is not associated with the pharmacy:

transmitting, to the electronic device via the network connection, information indicating the retail location of the pharmacy, and receiving, from the electronic device via the network connection, a confirmation to transfer the prescription to the retail location of the pharmacy.

16. The non-transitory computer-readable storage medium of claim 11, wherein processing the transfer of the prescription to the retail location of the pharmacy comprises:

transmitting a transfer request indicating the prescription to the retail location of the pharmacy.

\* \* \* \* \*